(12) United States Patent
Schenker et al.

(10) Patent No.: US 10,292,383 B2
(45) Date of Patent: May 21, 2019

(54) USE OF SURFACE-REACTED CALCIUM CARBONATE AS CARRIER FOR AGROCHEMICAL COMPOUNDS

(71) Applicant: Omya International AG, Oftringen (CH)

(72) Inventors: Michel Schenker, Schönenwerd (CH); Domenico Zocco, Zürich (CH); Patrick A.C. Gane, Rothrist (CH); Joachim Schoelkopf, Oberkulm (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 15/541,825

(22) PCT Filed: Jan. 13, 2016

(86) PCT No.: PCT/EP2016/050540
§ 371 (c)(1),
(2) Date: Jul. 6, 2017

(87) PCT Pub. No.: WO2016/113289
PCT Pub. Date: Jul. 21, 2016

(65) Prior Publication Data
US 2018/0014532 A1     Jan. 18, 2018

(30) Foreign Application Priority Data

Jan. 15, 2015   (EP) .................................... 15151353

(51) Int. Cl.
| | |
|---|---|
| *A01N 25/08* | (2006.01) |
| *A01N 37/38* | (2006.01) |
| *A01N 59/20* | (2006.01) |
| *A01N 43/84* | (2006.01) |

(52) U.S. Cl.
CPC .............. *A01N 25/08* (2013.01); *A01N 43/84* (2013.01); *A01N 59/20* (2013.01)

(58) Field of Classification Search
None
See application file for complete search history.

(56) References Cited

U.S. PATENT DOCUMENTS

| | | | |
|---|---|---|---|
| 9,744,107 B2 * | 8/2017 | Gane .................... | A61K 8/19 |
| 2004/0161388 A1 | 8/2004 | Liu et al. | |
| 2007/0248673 A1 | 10/2007 | Martinez et al. | |
| 2010/0010050 A1 | 1/2010 | Reizlein et al. | |
| 2012/0052023 A1 | 3/2012 | Gane et al. | |
| 2012/0295790 A1 | 11/2012 | Yan et al. | |

FOREIGN PATENT DOCUMENTS

| | | | |
|---|---|---|---|
| CN | 1751575 A | * | 3/2006 |
| CN | 1843119 A | | 10/2006 |
| EP | 2371766 A1 | | 10/2011 |
| EP | 2447213 A1 | | 5/2012 |
| EP | 2524898 A1 | | 11/2012 |
| JP | 11012116 A | * | 1/1999 |
| TW | 200603735 A | | 2/2006 |
| WO | 2010037753 A1 | | 4/2010 |
| WO | 2012025912 A1 | | 3/2012 |
| WO | 2013142473 A1 | | 9/2013 |
| WO | 2013180589 A1 | | 12/2013 |

OTHER PUBLICATIONS

Scheda dei dati di Sicurezza—Forum R 3B Flow Feb. 24, 2012, XP055191582, pp. 3-4.
The International Search Report dated Mar. 18, 2016 for PCT/EP2016/050540.
The Written Opinion of the International Searching Authority dated Mar. 18, 2016 for PCT/EP2016/050540.
Office Action dated Jan. 4, 2018 for Australian Application No. 2016208111.
Notice of Acceptance dated Mar. 26, 2018 for Australian Application No. 2016208111.
Office Action dated Jul. 16, 2018 for Canadian Application No. 2,953,879.
European Search Report dated Jun. 8, 2015 for European Application No. 15151353.8.
Office Action dated Apr. 5, 2018 for Russian Application No. 2017128805.
Search Report dated Apr. 5, 2018 for Russian Application No. 2017128805.
Office Action dated Sep. 10, 2016 for Taiwanese Application No. 104143544.
International Preliminary Report on Patentability dated Jul. 27, 2017 for Application No. PCT/EP2016/050540.

* cited by examiner

*Primary Examiner* — Alton N Pryor
(74) *Attorney, Agent, or Firm* — Amster, Rothstein & Ebenstein LLP

(57) ABSTRACT

The present invention relates to the use of surface-reacted calcium carbonate-containing minerals and/or surface-reacted precipitated calcium carbonates as solid particulate carriers to enhance the efficacy of agrochemical compounds loaded onto of said carriers.

24 Claims, 5 Drawing Sheets

USE OF SURFACE-REACTED CALCIUM CARBONATE AS CARRIER FOR AGROCHEMICAL COMPOUNDS

CROSS-REFERENCE TO RELATED APPLICATIONS

This is a U.S. national phase of PCT Application No. PCT/EP2016/050540, filed Jan. 13, 2016, which claims priority to European Application No. 15151353.8, filed Jan. 15, 2015.

The present application relates to the use of a particulate solid carrier to enhance the efficacy of an agrochemical compound which is loaded onto said carrier.

Agrochemical compounds are widely used in agriculture to improve the cultivation of useful plants. Many of these agrochemical compounds are known as crop protection products which may be used to protect plants from damaging influences such as weeds, plant diseases or insects. Crop protection products may include, for example, bactericides, fungicides, acaricides, insecticides, molluscicides, nematicides, rodenticides, avicides, and herbicides. Another group of agrochemical compounds is used to promote or regulate plant growth and includes fertilizers, soil additives, micronutrients and phytohormones.

In order to satisfy the needs of a constantly growing world population having a constantly growing demand for food, the use of agrochemical compounds has become indispensable. To cope with these growing demands, there have been several attempts to enhance the efficacy of agrochemical compounds.

Apart from the synthesis of novel compounds, the provision of synergistic compositions of known compounds represents one major principle in efficacy enhancement of agrochemical compounds, meaning that a combination of two or more such compounds produces an effect greater than the sum of their individual effects. Apart from that, the combination of two or more active compounds (e.g., two or more fungicides) allows for the prevention of new resistance.

For example, WO 2013/180589 A1 discloses a fungicidal composition comprising a mixture of dimethomorph and propamocarb hydrochloride in the form of a suspension concentrate which was found to provide a synergistic effect. As another example, WO 2012/025912 A1 discloses a composition comprising a combination of a morpholine fungicide (e.g., dimethomorph), a phthalimide fungicide (e.g., folpet) and a phosphorus containing fungicide (e.g., fosetyl-aluminum).

The development of specific formulations represents another major principle to improve the overall performance of a given agrochemical compound. Many of these formulations are designed to provide a sustained release profile of the agrochemical compound in order to prolong the efficacy.

For example, US 2012/0295790 A1 relates to a pesticidal composition comprising microcapsules which contain a pesticidal active ingredient and a suitable carrier and to a method of controlling pests comprising the application of an effective amount of such a pesticidal composition within a locus where pests are or are expected to be present. Said microcapsules exhibits sustained-release properties. Likewise, WO 2010/037753 A1 discloses a controlled release active agent carrier. Said carrier comprises a surface-reacted natural or synthetic calcium carbonate and one or more active agents.

However, it would be desirable to further improve the overall performance of agrochemical compounds which includes, on the one hand, enhancement of the efficacy of such compounds (e.g., the fungicidal activity of a fungicide) and, on the other hand, improve the user comfort (e.g., easily manageable formulations which, for example, may require a less frequent application of the formulation). Especially for poorly water soluble active agents an improved efficacy would be desirable.

In this respect, one object of the present invention may be seen in the provision of formulations which support the enhancement of the efficacy of agrochemical compounds.

Another object may be seen in the provision of formulations containing agrochemical compounds which can be applied less frequently and/or at lower overall dosage without significantly affecting the overall performance.

Another object may be seen in the provision of formulations containing agrochemical compounds which are enhanced to be equally efficient at lower overall costs.

Still another object of the present invention may be seen in the provision of more user-friendly formulations containing agrochemical compounds.

The foregoing and other problems may be solved by the subject-matter as defined herein in the independent claims.

A first aspect of the present invention relates to the use of a particulate solid carrier to enhance the efficacy of an agrochemical compound loaded onto said carrier;

characterized in that the particulate solid carrier comprises a surface-reacted calcium carbonate-containing mineral and/or a surface-reacted precipitated calcium carbonate.

The inventors surprisingly found that surface-reacted calcium carbonate-containing minerals and/or surface-reacted precipitated calcium carbonates may be used as solid particulate carriers to enhance the efficacy of agrochemical compounds loaded onto said carriers. Said surface-reacted calcium carbonate-containing minerals may be obtained by contacting calcium carbonate-containing minerals (e.g., marble) in an aqueous medium with carbon dioxide and with at least one water soluble acid (e.g., phosphoric acid). A similar process may be used to prepare surface-reacted precipitated calcium carbonates. Enhanced efficacy herein means that the efficacy of an agrochemical compound (e.g., the fungicidal activity of a fungicide) is greater compared with the agrochemical compound in pure form and in the absence of said carrier if applied under identical conditions.

Another aspect of the present invention relates to a composition comprising:

(a) at least one agrochemical compound; and
(b) a particulate solid carrier;

characterized in that said at least one agrochemical compound is a fungicide selected from the group consisting of benalaxyl, kiralaxyl, furalaxyl, metalaxyl, mefenoxam, oxadixyl, ofurace, dimethomorph, flumorph, pyrimorph, benthiavalicarb, iprovalicarb, valifenalate, mandipropamid; and the particulate solid carrier comprises a surface-reacted calcium carbonate-containing mineral and/or a surface-reacted precipitated calcium carbonate; and the agrochemical compound being loaded onto said particulate solid carrier.

The following terms used throughout the present application shall have the meanings set forth hereinafter:

A "carrier" in the meaning of the present application is to be understood as a substance which may be loaded with a second substance (e.g., an agrochemical compound) for the purpose of transporting said second substance to a target environment.

Where in this application it is described that a compound (e.g., the agrochemical compound) is "loaded onto" or "coated onto" a (particulate) carrier this means that said compound may be generally present on all sites of a carrier particle which are directly accessible from the outside of said particle. These sites include the outer surface of a carrier particle as well as pores or cavities being accessible from the outer surface.

The term "particulate" in the meaning of the present application refers to materials composed of a plurality of particles. Said plurality of particles may be defined, for example, by its particle size distribution.

The term "solid" refers to a physical state of a material. Unless indicated otherwise, this physical state is to be observed at a temperature of 20° C.

Unless specified otherwise, the term "efficacy" of an agrochemical compound is to be understood as the capacity for a beneficial effect caused by that agrochemical compound. Where a specific substance (e.g., a carrier) is used to "enhance the efficacy" of an agrochemical compound, this means that the beneficial effect caused by that agrochemical compound is higher when observed in the presence of said specific substance (e.g., the carrier) than that of the identical agrochemical compound observed in the absence of said specific substance (e.g., the carrier) and under identical or comparable conditions, preferably identical locus, reference parameter, dose, period of application, and ambient conditions. The skilled person very well knows the beneficial effect typically associated with a specific agrochemical compound. For example, the beneficial effect of a crop protection product or pesticide, such as a fungicide, may be tested under the EPPO guidelines which provide guidance on how to conduct field trials. The two parameters considered are:
 (i) PESSEV=the pest severity (i.e. the intensity) determined as infected area per bunch or leaf in %; and
 (ii) PESINC=the pest incidence (i.e. the frequency) determined in % of bunches and leaves infected.

These two parameters can be used to calculate the efficacy of an agrochemical composition as follows:

PESSEV efficacy [%]=(PESSEV$_{untreated}$−PESSEV$_{treated}$)/PESSEV$_{untreated}$×100

PESINC efficacy [%]=(PESINC$_{untreated}$−PESINC$_{treated}$)/PESINC$_{untreated}$×100.

Unless specifically stated otherwise, the "efficacy" in the meaning of the present invention shall include both the PESSEV efficacy and the PESINC efficacy. The "absolute water solubility" of a compound is to be understood as the maximum concentration of a compound in water where one can observe a single phase mixture at 20° C. under equilibrium conditions. The absolute water solubility is given in g compound per 100 g water.

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are bigger and 50 wt.-% are smaller than that particle size. For the purpose of the present invention, the particle size is specified as weight median particle size $d_{50}$ unless indicated otherwise. Particle sizes were determined by using a Sedigraph™ 5100 instrument of Micromeritics Instrument Corporation. The method and the instrument are known to the skilled person and are commonly used to determine the particle size of fillers and pigments. The measurements were carried out in an aqueous solution of 0.1 wt.-% $Na_4P_2O_7$.

The "particle size" of surface-reacted calcium carbonate herein is described as volume-based particle size distribution. For determining the volume-based particle size distribution, e.g., the volume-based median particle diameter ($d_{50}$) or the volume-based top cut particle size ($d_{98}$) of surface-reacted calcium carbonate, a Malvern Mastersizer 2 000 Laser Diffraction System with a defined RI of 1.57 and iRI of 0.005 and Malvern Application Software 5.60 was used. The measurement was performed with an aqueous dispersion. For this purpose, the samples were dispersed using a high-speed stirrer. The weight determined particle size distribution may correspond to the volume determined particle size if the density of all the particles is equal.

The "specific surface area" (expressed in $m^2/g$) of a material as used throughout the present document can be determined by the Brunauer Emmett Teller (BET) method with nitrogen as adsorbing gas and by use of a Gemini V instrument from Micromeritics. The method is well known to the skilled person and defined in ISO 9277:1995. Samples are conditioned at 250° C. for a period of 30 min prior to measurement. The total surface area (in $m^2$) of said material can be obtained by multiplication of the specific surface area (in $m^2/g$) and the mass (in g) of the material.

In the context of the present invention, the term "pore" is to be understood as describing the space that is found between and/or within particles, i.e. that is formed by the particles as they pack together under nearest neighbor contact (interparticle pores), such as in a powder or a compact and/or the void space within porous particles (intraparticle pores), and that allows the passage of liquids under pressure when saturated by the liquid and/or supports absorption of surface wetting liquids.

The "intraparticle intruded specific pore volume" according to the present invention can be calculated from a mercury intrusion porosimetry measurement and describes the measured pore volume that is found inside the pigment particles per unit mass of sample containing the particles. The intruded total specific void volume represents the sum of all the individual pore volumes, which can be intruded by mercury, per unit mass of the sample can be measured by mercury porosimetry using a Micrometrics Autopore IV mercury porosimeter. An exemplary mercury porosimetry experiment entails the evacuation of a porous sample to remove trapped gases, after which the sample is surrounded with mercury. The amount of mercury displaced by the sample allows calculation of the sample's bulk volume, $V_{bulk}$. Pressure is then applied to the mercury so that it intrudes into the sample through pores connected to the external surface. The maximum applied pressure of mercury can be 414 MPa, equivalent to a Laplace throat diameter of 0.004 μm. The data can be corrected using Pore-Comp (P. A. C. Gane et al. "Void Space Structure of Compressible Polymer Spheres and Consolidated Calcium Carbonate Paper-Coating Formulations", Industrial and Engineering Chemistry Research 1996, 35 (5):1753-1764) for mercury and penetrometer effects, and also for sample compression. By taking the first derivative of the cumulative intrusion curves the pore size distributions based on equivalent Laplace diameter, inevitably including the effect of pore-shielding when present, are revealed. The intruded total specific void volume corresponds to the void volume per unit mass of the sample determined by mercury porosimetry.

If necessary, the "solids content" of a suspension given in wt.-% in the meaning of the present invention can be determined using a Moisture Analyzer HR73 from Mettler-Toledo (T=120° C., automatic switch off 3, standard drying) with a sample size of 5 to 20 g.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt.-%, preferably less than or equal to 0.5 wt.-%, more preferably less than or equal to 0.2 wt.-%, and most preferably between 0.03 and 0.07 wt.-%, based on the total weight of the dried material.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

Advantageous embodiments of the inventive use of the particulate solid carrier are defined in the corresponding subclaims.

According to one embodiment of the present invention, the agrochemical compound is selected from fungicides, herbicides, insecticides, fertilizers, micronutrients, phytohormones, and mixtures thereof, preferably the agrochemical compound is a fungicide, more preferably a fungicide selected from metalaxyl and dimethomorph, and most preferably dimethomorph.

According to another embodiment of the present invention, the agrochemical compound has an absolute water solubility at 20° C. of less than 10 g/l, preferably less than 1.0 g/l, and most preferably less than 0.1 g/l.

According to another embodiment of the present invention, the particulate solid carrier is used in a weight ratio of from 1 000:1 to 1:1, preferably 500:1 to 2:1, and most preferably 200:1 to 3:1 on a dry weights basis relative to the weight of the agrochemical compound.

According to another embodiment of the present invention, the particulate solid carrier is used to enhance the efficacy of an agrochemical compound loaded onto said carrier in an aqueous formulation, preferably in an aqueous formulation with the particulate solid carrier being present in an amount of from 0.5 to 75 wt.-%, more preferably 1 to 60 wt.-%, even more preferably 2 to 50 wt.-%, and most preferably 5 to 25 wt.-%, based on the total weight of the aqueous formulation.

According to another embodiment of the present invention, the surface-reacted calcium carbonate-containing mineral is a reaction product obtainable by contacting a calcium carbonate-containing mineral in an aqueous medium with carbon dioxide and with at least one water soluble acid, wherein the carbon dioxide is formed in situ and/or is supplied from an external source.

According to another embodiment of the present invention, the at least one water soluble acid is selected from:
(i) acids having a $pK_a$ value of 0 or less at 20° C. (strong acids) or having a $pK_a$ value from 0 to 2.5 at 20° C. (medium strong acids); and/or
(ii) acids having a $pK_a$ of greater than 2.5 and less than or equal to 7 at 20° C. (weak acids), wherein at least one water soluble salt, which in the case of a hydrogen-containing salt has a $pK_a$ of greater than 7 and the salt anion of which is capable of forming water insoluble calcium salts, is additionally provided.

According to another embodiment of the present invention, the surface-reacted precipitated calcium carbonate is a reaction product obtainable by:
(a) providing precipitated calcium carbonate;
(b) providing $H_3O^+$ ions;
(c) providing at least one anion being capable of forming water insoluble calcium salts, said anion being solubilized in an aqueous medium; and
(d) contacting the precipitated calcium carbonate of step (a) with said $H_3O^+$ ions of step (b) and with said at least one anion of step (c) to form a slurry of surface-reacted precipitated calcium carbonate;
characterized in that an excess of solubilized calcium ions is provided during step (d); and
said surface-reacted precipitated calcium carbonate comprises an insoluble and at least partially crystalline calcium salt of said anion formed on the surface of at least part of the precipitated calcium carbonate provided in step (a).

According to another embodiment of the present invention:
(i) the $H_3O^+$ ions of step (b) are provided by addition of a water soluble acid or acidic salt which simultaneously serves to provide all or part of said excess solubilized calcium ions, preferably selected from the group comprising sulfur-comprising acids, such as sulfuric acid, hydrochloric acid, perchloric acid, formic acid, lactic acid, acetic acid, nitric acid, and acidic salts thereof, such as water soluble calcium acidic salts thereof;
(ii) the anion of step (c) is selected from one or more of the following: phosphate-comprising anions such as $PO_4^{3-}$ and $HPO_4^{2-}$, oxalate anions ($C_2O_4^{2-}$), carbonate-comprising anions in the form of $CO_3^{2-}$, phosphonate anions, succinate anions or fluoride anions; and/or
(iii) the excess of solubilized calcium ions is provided by addition of a water soluble neutral or acidic calcium salt, preferably selected from one or more of the following sources: $CaCl_2$ or $Ca(NO_3)_2$.

According to another embodiment of the present invention:
(i) the calcium carbonate-containing mineral is selected from the group consisting of marble, chalk, dolomite, limestone, and mixtures thereof and/or
(ii) the precipitated calcium carbonate is selected from the group consisting of precipitated calcium carbonates having an aragonitic, vateritic or calcitic crystal form, and mixtures thereof.

According to another embodiment of the present invention, the particulate solid carrier has a $d_{50}$ of from 2 to 50 μm, preferably 2.5 to 45 µm, more preferably 3 to 43 µm, and most preferably 3.5 to 40 µm.

According to another embodiment of the present invention, the particulate solid carrier has a specific surface area of from 10 to 200 m$^2$/g, more preferably 20 to 100 m$^2$/g, and most preferably 25 to 75 m$^2$/g.

According to another embodiment of the present invention, the particulate solid carrier has an intraparticle intruded specific pore volume within the range of 0.15 to 1.3 cm$^3$/g, preferably of 0.3 to 1.25 cm$^3$/g, and most preferably of 0.4 to 1.22 cm$^3$/g, calculated from a mercury intrusion porosimetry measurement.

According to another embodiment of the present invention, the agrochemical compound is a fungicide used in the prevention or treatment of a fungus or fungus-like organism on a plant host.

According to another embodiment of the present invention, the fungus or fungus-like organism preferably is an oomycete, preferably *Perenosporales*, and most preferably *Plasmopara viticola*.

According to another embodiment of the present invention, said plant host is selected from potato, tomato, corn, tobacco and grapevine, and preferably is grapevine.

According to another embodiment of the present invention, the agrochemical compound loaded onto said carrier is used together with a copper source, preferably tribasic copper sulfate or tribasic copper chloride, and most preferably tribasic copper sulfate.

According to another embodiment of the present invention, the efficacy is the PESSEV efficacy and/or PESINC efficacy.

According to another embodiment of the inventive composition, said composition further comprises a copper source, preferably tribasic copper sulfate or tribasic copper chloride, and most preferably tribasic copper sulfate.

In the following, preferred embodiments of the inventive use of the particulate solid carrier to enhance the efficacy of an agrochemical compound will be discussed in more detail. It is to be understood that these details and embodiments also apply to the inventive composition comprising at least one agrochemical compound and said particulate solid carrier.

(a) The Particulate Solid Carrier

The term "surface-reacted" (e.g., surface reacted calcium carbonate-containing mineral or surface-reacted precipitated calcium carbonate) in the meaning of the present application shall be used to indicate that a material has been subjected to a process comprising partial dissolution of said material upon acidic treatment (e.g., by use of water soluble free acids and/or acidic salts) in aqueous environment followed by a crystallization process which may occur in the absence or presence of further crystallization additives. The term "acid" as used herein refers to an acid in the meaning of the definition by Brønsted and Lowry (e.g., $H_2SO_4$, $HSO_4^-$), wherein the term "free acid" refers only to those acids being in the fully protonated form (e.g., $H_2SO_4$).

The surface-reacted calcium carbonate-containing mineral and/or the surface-reacted precipitated calcium carbonate used according to the present invention has a surface which differs from the surface of a corresponding untreated calcium carbonate-containing mineral and/or precipitated calcium carbonate, respectively, and which provides unique properties to the material.

Although less common, a "surface-reacted" material may be additionally or alternatively characterized by an increased intraparticle intruded specific pore volume as compared to the untreated starting material (i.e. calcium carbonate-containing mineral or precipitated calcium carbonate). Said increased pore volume or porosity is a result of the dissolution and recrystallisation process during its formation. Usually, the starting materials do not show any or only low internal porosity.

The unloaded particulate solid carrier according to the present invention may have a specific surface area of from 10 to 200 m$^2$/g, more preferably 20 to 100 m$^2$/g, and most preferably 25 to 75 m$^2$/g, measured using nitrogen and the BET method according to ISO 9277.

According to one embodiment, the unloaded particulate solid carrier may have a volume median grain diameter $d_{50}$ of 2 to 50 µm, preferably 2.5 to 45 µm, more preferably 3 to 43 µm, and most preferably 3.5 to 40 µm.

Preferably, the unloaded surface-reacted calcium carbonate has an intraparticle intruded specific pore volume within the range of 0.15 to 1.3 cm$^3$/g, preferably of 0.3 to 1.25 cm$^3$/g, and most preferably of 0.4 to 1.22 cm$^3$/g, calculated from mercury intrusion porosimetry measurement as described herein. The total pore volume seen in the cumulative intrusion data can be separated into two regions with the intrusion data from 214 µm down to about 1 to 4 µm showing the coarse packing of the sample between any agglomerate structures contributing strongly. Below these diameters lies the fine interparticle packing of the particles themselves. If they also have intraparticle pores, then this region appears bimodal. The sum of these three regions gives the total overall pore volume of the powder, but depends strongly on the original sample compaction/settling of the powder at the coarse pore end of the distribution. Further details with respect to the porosity or the intraparticle intruded specific pore volume of the surface-reacted calcium carbonate can be found in WO 2010/037753.

Surface-Reacted Calcium Carbonate-Containing Mineral:

The term "calcium carbonate-containing mineral" in the meaning of the present application is to be understood as a material of natural origin containing calcium carbonate and having an ordered atomic structure, such as marble, chalk, dolomite, or limestone. The calcium carbonate-containing mineral according to the present invention is used in a comminuted form, preferably in ground form, to provide the desired particle size distribution.

The surface-reacted calcium carbonate-containing mineral used according to the present invention is a reaction product of calcium carbonate-containing mineral with carbon dioxide and at least one water soluble acid in an aqueous medium, wherein the carbon dioxide is formed in situ by the acid treatment and/or is supplied from an external source.

The expression "acid treatment" in the meaning of the present invention refers to the reaction of the calcium carbonate-containing mineral or precipitated calcium carbonate and the at least one water soluble acid in the aqueous medium. By this reaction carbon dioxide can be formed in situ in the aqueous medium.

A calcium carbonate-containing mineral (GCC) is understood to be a naturally occurring form of calcium carbonate, mined from sedimentary rocks such as limestone or chalk, or from metamorphic marble rocks. Calcium carbonate is known to exist mainly as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Natural calcium carbonate is almost exclusively of the calcitic polymorph, which is said to be trigonal-rhombohedral and represents the most stable of the calcium carbonate polymorphs. The source of the calcium carbonate may comprise further naturally occurring components such as magnesium carbonate, alumino silicate etc. The term "source" of the calcium carbonate in the meaning of the present invention refers to the naturally occurring mineral from which the calcium carbonate is obtained.

According to one embodiment of the present invention, the calcium carbonate-containing mineral is selected from the group consisting of marble, chalk, dolomite, limestone, and mixtures thereof.

According to one embodiment of the present invention, the calcium carbonate-containing mineral is obtained by dry grinding. According to another embodiment of the present invention, the calcium carbonate-containing mineral is obtained by wet grinding and optionally subsequent drying.

In general, the grinding step can be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate-containing mineral comprises a wet calcium carbonate-containing mineral, the grinding step may be performed under conditions such that autogenous grinding takes place and/or by horizontal ball milling, and/or other such processes known to the skilled man. It is to be noted that the same grinding methods can be used for dry grinding the calcium carbonate-containing mineral. The wet processed calcium carbonate-containing mineral thus obtained may be washed and dewatered by well-known processes, e.g. by flocculation, filtration or forced evaporation prior to drying. The subsequent step of drying may be carried out in a single step such as spray drying, or in at least two steps. It is also common that such a mineral material is subjected to a beneficiation step (such as a flotation, bleaching or magnetic separation step) to remove impurities.

In a preferred embodiment, the calcium carbonate-containing mineral is ground prior to its conversion into the surface-reacted form. The grinding step can be carried out with any conventional grinding device such as a grinding mill known to the skilled person.

In a preferred process, the calcium carbonate containing mineral, either finely divided, such as by grinding, or not, is suspended in water to produce a slurry. Preferably, the slurry has a solids content within the range of from 1 to 80 wt.-%, more preferably 3 to 60 wt.-%, and even more preferably 5 to 40 wt.-%, based on the total weight of the slurry.

In a next step, at least one water soluble acid is added to the aqueous suspension containing the calcium carbonate-containing mineral or precipitated calcium carbonate. In general, the at least one acid can be any water soluble free acid selected from strong acids, medium strong acids, or weak acids, or mixtures thereof, generating $H_3O^+$ ions under the preparation conditions.

According to one embodiment, the at least one water soluble acid is a free acid selected from strong acids having a $pK_a$ of 0 or less at 20° C. According to another embodiment, the at least one water soluble acid is a free acid selected from medium strong acids having a $pK_a$ value from 0 to 2.5 at 20° C. If the $pK_a$ at 20° C. is 0 or less, the acid is preferably selected from sulfuric acid, hydrochloric acid, or mixtures thereof. If the $pK_a$ at 20° C. is from 0 to 2.5, the acid is preferably selected from $H_2SO_3$, $H_3PO_4$, oxalic acid, or mixtures thereof. According to a preferred embodiment, the least one water soluble acid is $H_3PO_4$.

In accordance with the present invention, $pK_a$ is the symbol representing the negative $\log_{10}$ of the acid dissociation constant associated with a given ionisable hydrogen in a given acid and is indicative for the natural degree of dissociation of this hydrogen from this acid at equilibrium in water at a given temperature. Such $pK_a$ values may be found in reference textbooks such as Harris, D. C. "Quantitative Chemical Analysis: 3rd Edition", 1991, W.H. Freeman & Co. (USA), ISBN 0-7167-2170-8, or CRC Handbook of Chemistry and Physics, 1994-1995 75th edition, 8-43 to 8-55, CRC Press Inc., 1995.

Additionally or alternatively, the at least one water soluble acid can also be a water soluble acidic salt which is capable to generate $H_3O^+$ ions under the preparation conditions, for example, $HSO_4^-$ or $H_2PO_4^-$, being at least partially neutralized by a corresponding cation such as $Li^+$, $Na^+$ or $K^+$, or $HPO_4^{2-}$, being at least partially neutralized by a corresponding cation such as $Li^+$, $Na^+$, $K^+$, $Mg^{2+}$ or $Ca^{2+}$. Therefore, the at least one water soluble acid can also be a mixture of one or more water soluble acids and one or more water soluble acidic salts.

According to still another embodiment, the at least one water soluble acid is a weak acid having a $pK_a$ value of greater than 2.5 and less than or equal to 7 at 20° C. and having a corresponding anion formed which is capable of forming water soluble calcium salts. According to a preferred embodiment, the weak acid has a $pK_a$ value from 2.6 to 5 at 20° C., and more preferably the weak acid is selected from the group consisting of acetic acid, formic acid, propanoic acid, and mixtures thereof.

In case a weak acid is used, after addition of said acid to the aqueous suspension containing the calcium carbonate-containing mineral or precipitated calcium carbonate, at least one water soluble salt, which in the case of a hydrogen-containing salt has a $pK_a$ of greater than 7 at 20° C. and the salt anion of which is capable of forming water insoluble calcium salts, must be additionally added. The cation of said water soluble salt is preferably selected from the group consisting of potassium, sodium, lithium and mixtures thereof. In a more preferred embodiment, said cation is sodium. It is of note that depending on the charge of the anion, more than one of said cations may be present to provide an electrically neutral ionic compound. The anion of said water soluble salt is preferably selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water soluble salt addition may be performed dropwise or in one step. In the case of dropwise addition, this addition preferably takes place within a time period of 15 minutes. It is more preferred to add said salt in one step.

According to the present invention, the at least one water soluble acid may be selected from the group consisting of hydrochloric acid, sulfuric acid, sulfurous acid, phosphoric acid, citric acid, oxalic acid, acetic acid, formic acid, and mixtures thereof. Preferably the at least one water soluble acid is selected from the group consisting of hydrochloric acid, sulfuric acid, sulfurous acid, phosphoric acid, oxalic acid, $H_2PO_4^-$ being at least partially neutralized by a corresponding cation such as $Li^+$, $Na^+$ or $K^+$, $HPO_4^{2-}$ being at least partially neutralized by a corresponding cation such as $Li^+$, $Na^+$ $K^+$, $Mg^{2+}$ or $Ca^{2+}$, and mixtures thereof, more preferably the at least one water soluble acid is selected from the group consisting of hydrochloric acid, sulfuric acid, sulfurous acid, phosphoric acid, oxalic acid, or mixtures thereof, and most preferably, the at least one water soluble acid is phosphoric acid.

According to the present invention, the at least one water soluble acid may be a mixture of one or more water soluble acids. For example, the at least one water soluble acid is a mixture of phosphoric acid and citric acid. The one or more water soluble acids may be added simultaneously or successively.

The at least one water soluble acid can be added to the suspension as a concentrated solution or a more diluted solution. According to the present invention, the molar ratio of the at least one water soluble acid to the calcium carbonate-containing mineral or precipitated calcium carbonate may be from 0.01 to 0.6, preferably from 0.05 to 0.55, and more preferably from 0.1 to 0.5. As an alternative, it is also possible to add the at least one water soluble acid to the water before the calcium carbonate-containing mineral or precipitated calcium carbonate is suspended.

In a next step, the calcium carbonate-containing mineral is treated with carbon dioxide. The carbon dioxide can be formed in situ by the acid treatment and/or can be supplied from an external source. If a strong acid such as sulfuric acid or hydrochloric acid or a medium strong acid such as phosphoric acid is used for the acid treatment of the calcium carbonate-containing mineral, the carbon dioxide is automatically formed in a sufficient amount to achieve the required molar concentration. Alternatively or additionally, the carbon dioxide can be supplied from an external source.

Acid treatment and treatment with carbon dioxide can be carried out simultaneously which is the case when a strong or medium strong acid is used. It is also possible to carry out acid treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the acid treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably from 1:0.05 to 1:5.

The acid treatment step and/or the carbon dioxide treatment step may be repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted calcium carbonate-containing mineral as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

According to the present invention, the surface-reacted calcium carbonate-containing mineral may be obtained by a process comprising the steps of:
(a) providing a suspension of calcium carbonate-containing mineral;
(b) adding at least one water soluble acid having a $pK_a$ value of 0 or less at 20° C. or having a $pK_a$ value from 0 to 2.5 at 20° C. to the suspension of step (a); and
(c) treating the suspension of step (a) with carbon dioxide before, during or after step (b).

According to the present invention, at least one water soluble acid having a $pK_a$ value of 0 or less at 20° C. may be added in step (b) to the suspension of step (a). The at least one water soluble acid having a $pK_a$ value from 0 to 2.5 at 20° C. may be added in step (b) to the suspension of step (a).

The carbon dioxide used in step (c) can be formed in situ by the acid treatment of step (b) and/or can be supplied from an external source.

According to another embodiment of the present invention, the surface-reacted calcium carbonate-containing mineral may be obtained by a process comprising the steps of:
(a) providing a calcium carbonate-containing mineral;
(b) providing at least one water soluble acid;
(c) providing gaseous carbon dioxide;
(d) contacting said calcium carbonate-containing mineral of step (a) with the at least one water soluble acid of step (b) and with the carbon dioxide of step (c);
wherein
(i) the at least one water soluble acid of step (b) has a $pK_a$ of greater than 2.5 and less than or equal to 7 at 20° C. and a corresponding anion is formed capable of forming a water soluble calcium salt; and
(ii) following contacting the at least one water soluble acid with the calcium carbonate-containing mineral, at least one water soluble salt, which in the case of a hydrogen-containing salt has a $pK_a$ of greater than 7 at 20° C. and the salt anion of which is capable of forming water insoluble calcium salts, is additionally provided.

According to the present invention, the calcium carbonate-containing mineral may be reacted with the at least one water soluble acid and/or the carbon dioxide in the presence of at least one compound selected from the group consisting of silicate, magnesium oxide, citric acid, aluminium sulfate, aluminium nitrate, aluminium chloride, and mixtures thereof. These components can be added to an aqueous suspension comprising the calcium carbonate-containing mineral before adding the at least one water soluble acid and/or carbon dioxide.

The surface-reacted calcium carbonate-containing mineral to be used in the present invention may be provided in dry form or as a suspension.

According to the present invention, the surface-reacted calcium carbonate-containing mineral may comprise an insoluble, at least partially crystalline calcium salt of an anion of the at least one water soluble acid which is formed on the surface of the calcium carbonate-containing mineral or precipitated calcium carbonate. According to one embodiment, the insoluble, at least partially crystalline salt of an anion of the at least one water soluble acid covers the surface of the calcium carbonate-containing mineral at least partially, preferably completely. Depending on the employed at least one water soluble acid, the anion may be sulfate, sulfite, phosphate, citrate, oxalate, acetate and/or formate.

Surface-Reacted Precipitated Calcium Carbonate:

As already described hereinabove, the particulate solid carrier may also be a surface-reacted material prepared from precipitated calcium carbonate, i.e. surface-reacted precipitated calcium carbonate as described in EP 2 070 991 B1.

A "precipitated calcium carbonate" (PCC) in the meaning of the present application is a synthetic material and may be generally obtained by precipitation following a reaction of carbon dioxide and calcium hydroxide (hydrated lime) in an aqueous environment, or by precipitation in the presence of a calcium and a carbonate source in water. For example, precipitated calcium carbonate can be the product obtained by introducing calcium and carbonate salts (e.g., calcium chloride and sodium carbonate) into an aqueous environment. Such precipitated calcium carbonates may have a vateritic, calcitic or aragonitic structure and are described, for example, in EP 2 447 213 A1, EP 2 524 898 A1, EP 2 371 766 A1 and WO 2013/142473.

According to one embodiment of the present invention, the precipitated calcium carbonate is selected from the group consisting of precipitated calcium carbonates having aragonitic, vateritic or calcitic mineralogical crystal forms, and mixtures thereof.

For the purposes of the present invention, the surface-reacted precipitated calcium carbonate may be obtained by contacting precipitated calcium carbonate with $H_3O^+$ ions and with anions being solubilized in an aqueous medium and being capable of forming water insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acidic salt, and in absence of any further calcium ion or calcium ion generating source.

In one embodiment, a process to prepare surface-reacted precipitated calcium carbonate comprises the following steps:
(a) providing precipitated calcium carbonate;
(b) providing $H_3O^+$ ions;
(c) providing at least one anion being capable of forming water insoluble calcium salts, said anion being solubilized in an aqueous medium; and
(d) contacting the precipitated calcium carbonate of step (a) with said $H_3O^+$ ions of step (b) and with said at least one anion of step (c) to form a slurry of surface-reacted precipitated calcium carbonate;
characterized in that an excess of solubilized calcium ions is provided during step (d); and
said surface-reacted precipitated calcium carbonate comprises an insoluble and at least partially crystalline calcium salt of said anion formed on the surface of at least part of the precipitated calcium carbonate provided in step (a).

For the purpose of the present application, "insoluble" materials are defined as those which, when mixed with 100 ml of deionised water and filtered at 20° C. to recover the liquid filtrate, provide less than or equal to 0.1 g of recovered solid material following evaporation at 95 to 100° C. of 100 g of said liquid filtrate. "Soluble" materials are defined as materials leading to the recovery of greater than 0.1 g of solid material following evaporation at 95 to 100° C. of 100 g of said liquid filtrate. In order to assess whether a material is an insoluble or soluble material in the meaning of the present invention, the sample size is greater than 0.1 g, preferably 0.5 g or more.

Preferably, the slurry has a solids content within the range of from 1 to 80 wt.-%, more preferably 3 to 60 wt.-%, and even more preferably 5 to 40 wt.-%, based on the total weight of said slurry.

In said process, the $H_3O^+$ ions of step (b) may be provided by one or more of the following routes:
IB: addition of a water soluble acid or acidic salt of said anion;
IIB: addition of a water soluble acid or acidic salt which simultaneously serves to provide all or part of said excess solubilized calcium ions, i.e. by direct addition of soluble calcium ions and/or by dissolution of the starting material to liberate calcium ions.

In the case of route IIB, said water soluble acid or acidic salt which simultaneously serves to provide all or part of said excess solubilized calcium ions is preferably selected from the group comprising sulfur-comprising acids, such as sulfuric acid, hydrochloric acid, perchloric acid, formic acid, lactic acid, acetic acid, nitric acid, and acidic salts thereof, such as water soluble calcium acidic salts thereof.

The anion of step (c) may be selected from one or more of the following: phosphate-comprising anions such as $PO_4^{3-}$ and $HPO_4^{2-}$, oxalate anions ($C_2O_4^{2-}$), carbonate-comprising anions in the form of $CO_3^{2-}$, phosphonate anions, succinate anions or fluoride anions.

The excess solubilized calcium ions provided during step (d) may be provided by one or more of the following routes:
IA: addition of a water soluble neutral or acidic calcium salt;
IIA: addition of a water soluble acid or neutral or acidic non-calcium salt which generates a water soluble neutral or acidic calcium salt in situ.

In a preferred embodiment, said excess solubilized calcium ions are provided by route IA, more preferably they may be selected from one or more of the following sources: $CaCl_2$ or $Ca(NO_3)_2$.

In general, the foregoing process may also be used to produce surface-reacted calcium carbonate from calcium carbonate-containing mineral.

In another preferred embodiment, the precipitated calcium carbonate is ground prior to the conversion into the surface-reacted form. Said grinding step can be carried out with any conventional grinding device such as a grinding mill known to the skilled person.

(b) The Agrochemical Compound

According to the present invention, an agrochemical compound is loaded onto the inventive particulate solid carrier in order to enhance the efficacy of said agrochemical compound. The agrochemical compound may be selected from fungicides, herbicides, insecticides, fertilizers, micronutrients, phytohormones, and mixtures thereof, preferably the agrochemical compound may be a fungicide, more preferably a phenyl amide fungicide (PA fungicide) or a carboxylic acid amide fungicide (CAA fungicide), even more preferably a fungicide selected from benalaxyl, kiralaxyl, furalaxyl, metalaxyl, mefenoxam, oxadixyl, ofurace, dimethomorph, flumorph, pyrimorph, benthiavalicarb, iprovalicarb, valifenalate, mandipropamid, even more preferably metalaxyl and dimethomorph, and most preferably dimethomorph.

According to another preferred embodiment, the agrochemical compound is an herbicide having FRAC code 4 (target site code A1) or 40 (target site code H5) according to the FRAC code list 2014.

Suitable herbicides representing an agrochemical compound according to the present invention also include acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Flurochloridone, Fluroxypyr, Flurtamone, Fomesafen, Foramsulfuron, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. Preferred herbicides are Acetochlor, Atrazine, Dicamba, Glufosinate, Paraquat, glyphosate, 2,4-D and mixtures and combinations thereof.

Suitable fungicides representing an agrochemical compound according to the present invention also include acibenzolar-S-methyl, aldimorph, amisulbrom, anilazine, azaconazole, azoxystrobin, benalaxyl, benodanil, benomyl, benthiavalicarb, binapacryl, biphenyl, bitertanol, blasticidin-S, boscalid, bromuconazole, bupirimate, captafol, captan, carbendazim, carboxin, carpropamid, chloroneb, chlorothalonil, chlozolinate, copper, cyazofamid, cyflufenamid, cymoxanil, cyproconazole, cyprodinil, dichlofivanid, diclocymet, diclomezine, dicloran, diethofencarb, difenoconazole, diflumetorim, dimethirimol, dimethomorph, dimoxystrobin, diniconazole, dinocap, dithianon, dodemorph, dodine, edifenphos, enestrobin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, fiumorph, fluopicolide, fluoxastrobin, fluquinconazole, fiusilazole, fiusulfamide, flutolanil, fiutriafol, folpet, fosetyl-Al, fthalide, fuberidazole, furalaxyl, furametpyr, guazatine, hexaconazole, hymexazole, imazalil, imibenconazole, iminoctadine, iodocarb, ipconazole, iprobenfos (IBP), iprodione, iprovalicarb, isoprothiolane, isotianil, kasugamycin, kresoxim-methyl, laminarin, mancozeb, mandipropamid, maneb, material of biological, mepanipyrim, mepronil, meptyldinocap, metalaxyl, metalaxyl-M, metconazole, methasulfocarb, metiram, metominostrobin, metrafenone, mineral oils, organic oils, myclobutanil, naftifine, nuarimol, octhilinone, ofurace, origin, orysastrobin, oxadixyl, oxolinic acid, oxpoconazole, oxycarboxin, oxytetracycline, pefurazoate, penconazole, pencycuron, penthiopyrad, phophorous acid and, picoxystrobin, piperalin, polyoxin, potassium bicarbonate, probenazole, prochloraz, procymidone, propamocarb, propiconazole, propineb, proquinazid, prothiocarb, prothioconazole, pyraclostrobin, pyrazophos, pyribencarb, pyributicarb, pyrifenox, pyrimethanil, pyroquilon, quinoxyfen, quintozene (PCNB), salts, silthiofam, simeconazole, spiroxamine, streptomycin, sulfur, tebuconazole, teclofthalam, tecnazene (TCNB), terbinafine, tetraconazole, thiabendazole, thifluzamide, thiophanate, thiophanate-methyl, thiram, tiadinil, tolclofosmethyl, tolylfivanid, triadimefon, triadimenol, triazoxide, tricyclazole, tridemorph, trifloxystrobin, triflumizole, triforine, triticonazole, validamycin, valiphenal, vinclozolin, zineb, ziram, and zoxamide, and mixtures and combinations thereof. Further fungicides representing an agrochemical compound according to the present invention include 1-butyl-1-(2,4-dichlorophenyl)-2-(1,2,4-triazol-1-yl) ethanol (common name hexaconazole), 1-[(2-chlorophenyl)methyl]-1-(1,1-dimethylethyl)-2-(1,2,4-triazol-1-yl)ethanol, 1-(4-fluorophenyl)-1-(2-fluorophenyl)-2-(1,2,4-triazol-1-yl) ethanol (common name flutriafol), methyl (E)-2-[2-[6-(2-cyanophenoxy)pyrimidin-4-yloxy]phenyl]-3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)phenoxy]phenyl]-3-methoxyacrylate, methyl (E)-2-[2-[3-(phenyl-sulfonyloxy)phenoxy]phenyl]-3-methoxyacrylate, methyl (E)-2-[2-[3-[4-nitrophenoxy]phenoxy]phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]-3-methoxyacrylate, methyl (E)-2-[2-(3-methoxyphenoxy)phenyl]-3-methoxyacrylate, methyl (E)-2-[2-(2-phenylethen-1-yl)phenyl]-3-methoxyacrylate, methyl (E)-2-(2-[3,5-dichloro-phenoxy]pyridin-3-yl)-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxyphenoxy)phenyl]-3-methoxyacrylate, methyl (E)-2-[2-(3-iso-propyloxyphenoxy)phenyl]-3-methoxyacrylate, methyl (E)-2-[2-[3-(2-fluorophenoxy)phenoxy]phenyl]-3-methoxy acrylate, methyl (E)-2-[2-(3-ethoxyphenoxy)phenyl]-3-methoxyacrylate, methyl (E)-2-[2-(4-tert-butylpyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-(3-methylpyridin-2-yloxymethyl)phenyl]-3-methoxyacrylate, methyl (E)-2-[2-[6(2-methylphenoxy)pyrimidin-4-yloxy]phenyl]-3-methoxyacrylate, methyl (E)-2-[2-(5-bromopyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-

[2-[6-(2-chloropyridin-3-yloxy)pyrimidin-4-yloxy]phenyl]-3-methoxyacrylate, (E),(E)-methyl 2-[2-(5,6-dimethylpyrazin-2-ylmethyloximinomethyl)phenyl]-3-methoxyacrylate, (E)-methyl 2-{2-[6-(6-methylpyridin-2-yloxy)pyrimidin-4-yloxy]phenyl}-3-methoxyacrylate, (E),(E)-methyl 2-{2-[(3-methoxyphenyl)methyloximinomethyl]pheny}-3-methoxyacrylate, (E)-methyl 2-{2-[6-(2-azidophenoxy)pyrimidin-4-yloxy]phenyl}-3-methoxyacrylate, (E),(E)-methyl 2-{2-[6-phenylpyrimidin-4-yl)methyloximinomethyl]pheny}-3-methoxyacrylate, (E),(E)-methyl 2-{2-[(4-chlorophenyl)methyloximinomethyl]phenyl}-3-methoxyacrylate, (E)-methyl 2-{2-[6-(2-n-propylphenoxy)-1,3,5-triazin-4-yloxy]phenyl}-3-methoxyacrylate, (E),(E)-methyl 2-{2-[(3-nitrophenyl)methyloximinomethyl]phenyl}-3-methoxyacrylate, (RS)-4-(4-chlorophenyl)-2-phenyl-2-(1H-1,2,4-triazol-1-ylmethyl)butyronitrile, 1-[(2RS,4RS;2RS,4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)-quinazolin-4(3H)-one, (RS)-2,2-dimethyl-3-(2-chlorobenzyl)-4-(1H-1,2,4-triazol-1-yl)butan-3-ol. The most preferred fungicide according to the present invention is dimethomorph.

Suitable insecticides representing an agrochemical compound according to the present invention include kerosene or borax, botanicals or natural organic compounds (nicotine, pyrethrin, strychnine and rotenone), chorinated hydrocarbon (DDT, lindane, chlordane), organophosphates (malathion and diazinon), carbamates (carbaryl and propoxur), fumigants naphthalene (mothballs) and benzene, synthetic pyrethroids, and mixtures and combinations thereof.

Suitable fertilizers representing an agrochemical compound according to the present invention include inorganic and organic fertilizers and mixtures thereof. The fertilizers may also comprise micronutrients which include iron, zinc, manganese, magnesium, copper, calcium, boron, cobalt, iron (sulfur), sulfate, chlorine and molybdenum. A micronutrient herein is a nutrient whose natural level found in plants is 0.01 wt.-% or less. The sources of the micronutrients are, for example, oxides, hydroxides, salts, carbonates, chlorides, nitrates, sulfates, sequestrates, chelates and complexes. Typical oxides include $FeO$, $Fe_2O_3$, $Fe_3O_4$, $ZnO$, $ZnO_2$, $CaO$, $CaO_2$, $MnO$, $MnO_2$, $Mn_2O_3$, $Mn_2O_7$, $Mn_3O_4$, $MgO$, $CuO$, $Cu_2O$, $B_2O_3$, $MoO$, $MoO_2$, $MoO_3$, $Mo_2O_3$, $Mo_2O_5$, $CoO$, and $Co_3O_4$.

Suitable phytohormones representing an agrochemical compound according to the present invention include auxins, abscisics, brassinosteroids, jasmonates, traumatic acids, cytokinins, isoflavinoids, gibberelins and ethylene, or a mixture thereof. Examples of phytohormones also include salicylic acid, acetyl salicylic acid, indole acetic acid, gibberellic acid, gallic acid, cytokinin, abscisic acid, and ethylene.

It is especially preferred that the agrochemical compound used according to the present invention has an absolute water solubility at 20° C. of less than 10 g/l, preferably less than 1.0 g/l, and most preferably less than 0.1 g/l. The improved efficacy is especially observed and especially advantageous for agrochemical compounds having a poor water solubility as these compounds may have a tendency to be less effective in comparison to compounds being readily soluble in water.

(c) The Agrochemical Composition and its Use

The present invention relates to the use of a particulate solid carrier to enhance the efficacy of an agrochemical compound loaded onto said carrier, wherein the particulate solid carrier comprises or is a surface-reacted calcium carbonate-containing mineral and/or a surface-reacted precipitated calcium carbonate.

Furthermore, the present invention relates to a composition comprising:
(a) at least one agrochemical compound; and
(b) a particulate solid carrier;
characterized in that said at least one agrochemical compound is a fungicide selected from the group consisting of benalaxyl, kiralaxyl, furalaxyl, metalaxyl, mefenoxam, oxadixyl, ofurace, dimethomorph, flumorph, pyrimorph, benthiavalicarb, iprovalicarb, valifenalate, mandipropamid; and
the particulate solid carrier comprises a surface-reacted calcium carbonate-containing mineral and/or a surface-reacted precipitated calcium carbonate; and
the agrochemical compound being loaded onto said particulate solid carrier.

It is to be understood that the embodiments relating to the inventive use described above and in the following also apply to the inventive composition.

According to the present invention, it may be preferred that the particulate solid carrier is a surface-reacted calcium carbonate-containing mineral and/or a surface-reacted precipitated calcium carbonate and does not comprise any compounds other than the agrochemical compound loaded onto said carrier.

Generally, the loading of the agrochemical compound onto the surface-reacted calcium carbonate carrier is effected by contacting the particulate carrier with a solution or suspension of the agrochemical compound in a suitable medium or solvent, for example acetone or water. After the coating or association with the agrochemical compound, the excess liquid may be removed, e.g. by filtration, and optionally dried. With respect to the drying of the loaded particulate carrier, it is preferred to apply a well controlled drying method, such as gentle spray drying or oven-drying. The surface and/or the accessible pores of the particulate carrier is/are partly or fully loaded or coated with agrochemical compound by the foregoing process or contacting step.

Alternatively, the agrochemical compound may be loaded onto said particulate solid carrier by means of:
i) incipient wetness technique, i.e. impregnating the particulate solid carrier with a solution of the agrochemical in a suitable mixer (e.g., a fluid bed mixer); or
(ii) hot melt impregnation technique, i.e. impregnating the particulate solid carrier with a melt of the agrochemical in a suitable heated mixer (e.g., a fluid bed mixer).

Therefore, in one embodiment the composition comprises:
(a) at least one agrochemical compound; and
(b) a particulate solid carrier;
characterized in that the particulate solid carrier comprises a surface-reacted calcium carbonate-containing mineral and/or a surface-reacted precipitated calcium carbonate; and
the agrochemical compound being loaded onto said particulate solid carrier by means of:
(i) solvent evaporation in a rotational evaporator; or
(ii) incipient wetness; or
(iii) hot melt impregnation technique.

Incipient wetness impregnation (abbreviated IW or IWI), also called capillary impregnation or dry impregnation, is a commonly used technique to load an active substance onto and into a porous and/or high surface area solid particulate material.

In the case of loading an active ingredient, such as an agrochemical compound, into a powder of porous particles the procedure is as follows:

The active is dissolved in an aqueous or organic solution. Then, the active containing solution is added to an amount of powder containing the same pore volume as the volume of the solution that was added. Capillary action draws the solution into the pores. The powder should be agitated or shaken to facilitate and accelerate liquid distribution. The powder can then be dried to drive off the volatile components within the solution, preferably under vacuum, depositing the active on the particles inner and outer surface. The concentration profile of the impregnated compound depends on the mass transfer conditions within the pores during impregnation and drying.

Hot melt impregnation is a commonly used technique to load meltable compounds onto and into a porous and or high surface area solid particulate material. Typically, the powder is heated to a temperature above the melting point of the active compound and then blended with a melt of the active compound in a heated suitable device such as an extruder or a ploughshare mixer, kneader or fluid bed mixer. The amount of molten active ingredient should be dosed in an amount below the available intra particle pore volume of the involved porous powder if the powdered form should be maintained.

The resulting loaded particulate carrier being loaded with one or more agrochemical compounds may be applied according to methods well-known in the art. It may be used in dry form, e.g. as granulate or powder or in liquid form, e.g. as a suspension, preferably an aqueous suspension. The suspension may be applied using a power sprayer, a manual sprayer, a watering can, sprinkler or an irrigation device. The dilution ratio is typically within a range of from 3:1 (water: loaded carrier) to 10 000:1, and preferably from 5:1 to 8 000:1. According to the present invention it is preferred that the particulate solid carrier is used to enhance the efficacy of an agrochemical compound loaded onto said carrier in an aqueous formulation or composition, preferably in an aqueous formulation with the particulate solid carrier being present in an amount of from 0.5 to 75 wt.-%, more preferably 1 to 60 wt.-%, even more preferably 2 to 50 wt.-%, and most preferably 5 to 25 wt.-%, based on the total weight of the aqueous formulation.

The loaded particulate carrier according to the present invention is usually diluted or suspended with water, and then depending on the variety of the agrochemical active ingredient and the intended use, the resulting suspension can be sprayed onto agricultural land, non-agricultural land such as forests, grasslands, golf courses, roadside trees, roads, road verges and marshes, or water systems such as ponds, reservoirs, rivers, watercourses and sewerage systems. The loaded particulate carrier may be applied to the area where control of plant growth is desired, prior to or after emergence of the target plants, for example by spraying onto the surface of the soil or onto the foliage of the plants.

The amount of the agrochemical compound applied is typically within a range from 0.001 kg/ha to 25 kg/ha, preferably 0.01 to 5 kg/ha, more preferably 0.1 to 2 kg/ha, and most preferably 0.2 to 1 kg/ha. The agrochemical composition containing the inventive particulate carrier loaded with one or more agrochemical compounds, preferably suspended in water may comprise further additives like surfactants, defoamers, diluents, solvents, compatibility agents, thickeners, drift control agents, dyes, fragrance, and chelating agents.

According to the present invention it is preferred that the particulate solid carrier is used in a weight ratio of from 1 000:1 to 1:1, preferably 500:1 to 2:1, and most preferably 200:1 to 3:1 on a dry weights basis relative to the weight of the agrochemical compound.

The improved efficacy provided according to the present invention preferably allows for a significantly reduced number of applications of the agrochemical compound to the site to be treated compared to the application of the identical agrochemical compound observed in the absence of the inventive particulate carrier under identical or comparable conditions. Preferably, the inventive formulation or composition needs to be applied 20% less frequently, preferably 30%, 40%, 50%, 60% or 70% less frequently in order to achieve the same efficacy observed for the identical agrochemical compound in the absence of the inventive particulate carrier under identical or comparable conditions. The inventive agrochemical formulation or composition may preferably be used together with or may comprise other agrochemical compositions, for example formulations or compositions containing a copper source such as tribasic copper sulfate or tribasic copper chloride, preferably tribasic copper sulfate.

In one embodiment of the present invention, the agrochemical compound loaded onto the carrier is used together with a copper source (e.g., tribasic copper sulfate or tribasic copper chloride), preferably in the prevention or treatment of a fungus or fungus-like organism (e.g., *Plasmopara viticola*) on a plant host. The use of a copper source as an additive may be useful to reduce the incidence of resistances against said agrochemical compound.

In cases where the agrochemical compound loaded onto the carrier is used together with a copper source, the application rate of said agrochemical compound may range from 0.001 kg/ha to 25 kg/ha, preferably 0.01 to 5 kg/ha, more preferably 0.1 to 2 kg/ha and most preferably 0.2 to 1 kg/ha, and the application rate of the copper source ranges from 0.001 kg/ha to 25 kg/ha, preferably 0.01 to 5 kg/ha, more preferably 0.1 to 2 kg/ha and most preferably 0.2 to 1 kg/ha. These application rates particularly may apply to cases where the agrochemical compound is dimethomorph and the copper source is tribasic copper sulfate.

For this purpose, said tribasic copper sulfate may preferably be used in the form of water soluble granules such as Cupravit® Bio Evolution from Bayer Crop Science. However, the copper source (e.g., tribasic copper sulfate or tribasic copper chloride) may also be used in the form of a wettable powder wherein the copper source is loaded onto or mixed with a solid carrier or substance (e.g., kaolinite).

The inventive formulation or composition containing a particulate solid carrier to enhance the efficacy of an agrochemical compound loaded onto said carrier, characterized in that the particulate solid carrier comprises a surface-reacted calcium carbonate-containing mineral and/or a surface-reacted precipitated calcium carbonate is especially suitable in the prevention or treatment of a fungus or fungus-like organism on a plant host with the agrochemical compound being a fungicide, wherein the fungus or fungus-like organism preferably is an oomycete, preferably *Perenosporales*, and most preferably *Plasmopara viticola*. The plant host may be potato, tomato, corn, tobacco or grapevine, and preferably is grapevine.

The term “efficacy” in the meaning of the present invention may refer to both the PESSEV efficacy (pest severity) and the PESINC efficacy (pest incidence) as defined hereinabove and takes into account untreated controls. In some embodiments according to the present invention, the term efficacy refers only to the PESSEV efficacy or the PESINC efficacy which may especially apply in cases where the agrochemical compound is dimethomorph.

Where a specific substance (e.g., a carrier) is used to “enhance the efficacy” of an agrochemical compound, this typically means that the beneficial effect caused by that agrochemical compound is greater when observed in the presence of said specific substance (e.g., the carrier) than that of the identical agrochemical compound observed in the absence of said specific substance (e.g., the carrier) and under identical or comparable conditions, preferably identical locus, reference parameter, dose, period of application, and ambient conditions.

However, according to an alternative embodiment, the term "enhance the efficacy" includes both the PESSEV efficacy and/or the PESINC efficacy and means that the beneficial effect caused by that agrochemical compound is greater than that of the identical agrochemical compound in commercial formulations and observed under identical or comparable conditions (identical locus, reference parameter, dose, period of application, and ambient conditions etc.). In cases where the agrochemical compound is selected from PA fungicides or CAA fungicides and particularly dimethomorph, these commercial formulations include Forum® R3B (FR3B) and Forum® 50 WP (F50), wherein Forum® 50 WP (F50) may be preferred.

EXAMPLES

Figure 1A:
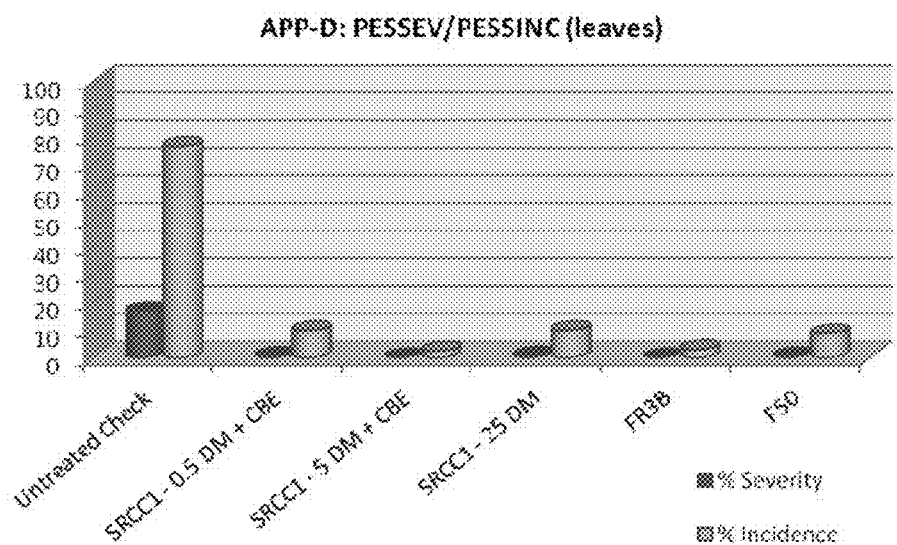
FIG. 1a: Results of the first assessment on leaves with regard to the pest severity PESSEV and the pest incidence PESINC after application D.
Figure 1B:
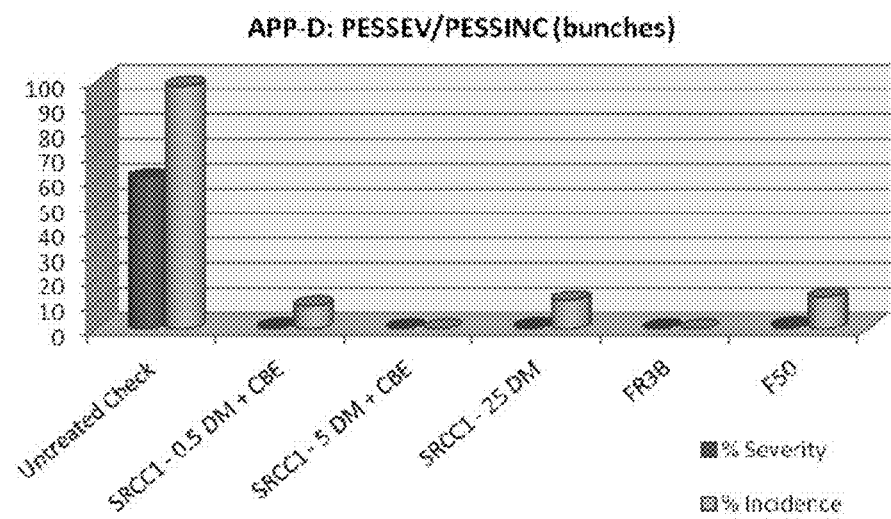
FIG. 1b: Results of the first assessment on bunches with regard to the pest severity PESSEV and the pest incidence PESINC after application D.
Figure 1C:
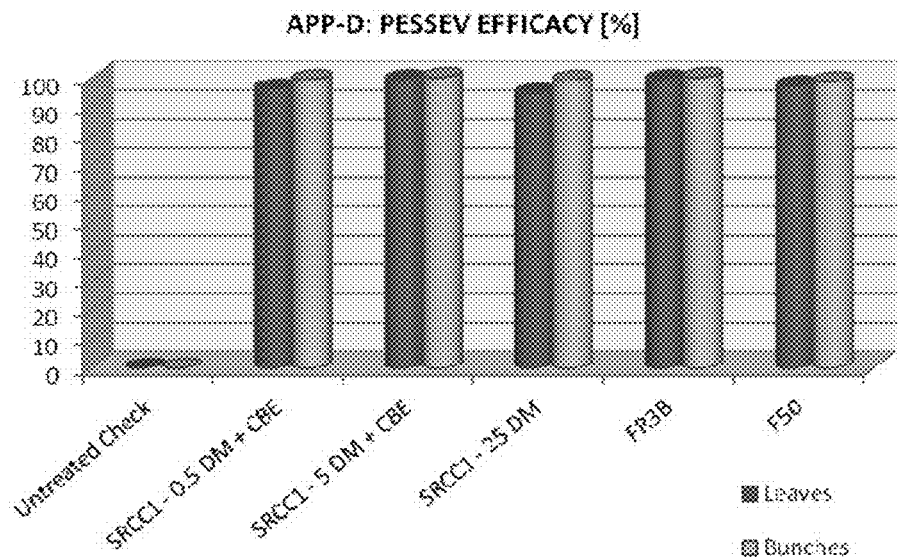
FIG. 1c: Results of PESSEV efficacy evaluation after application D.
Figure 2A:
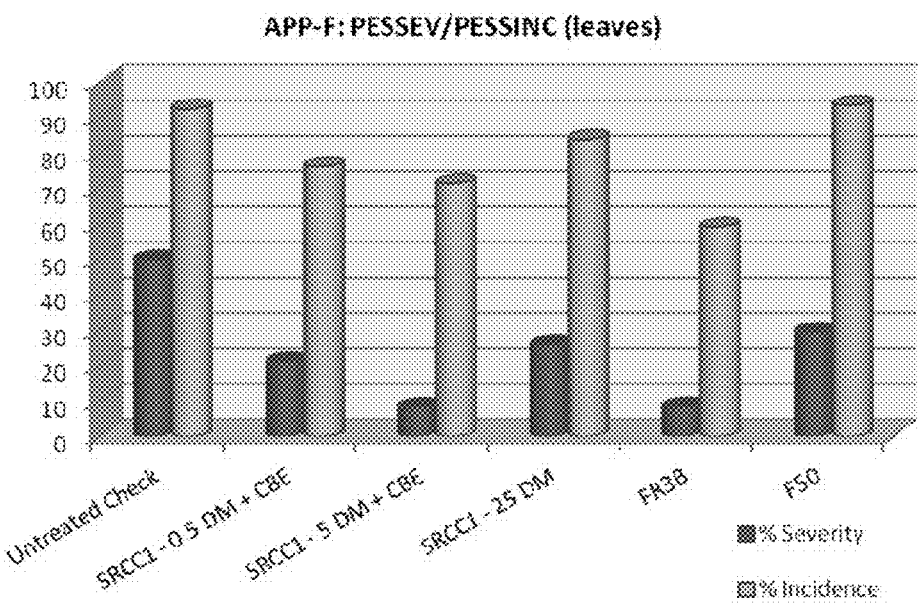
FIG. 2a: Results of the first assessment on leaves with regard to the pest severity PESSEV and the pest incidence PESINC after application F.
Figure 2B:
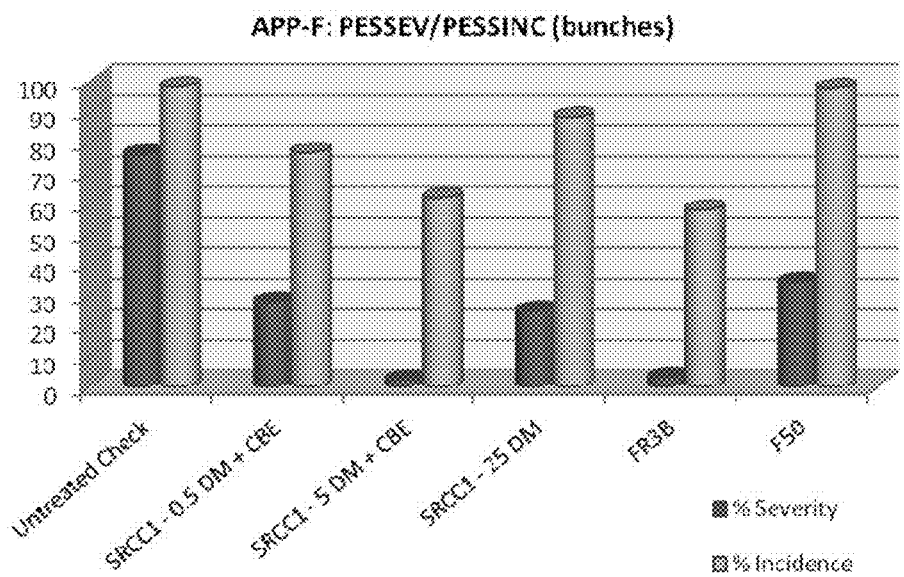
FIG. 2b: Results of the first assessment on bunches with regard to the pest severity PESSEV and the pest incidence PESINC after application F.
Figure 2C:
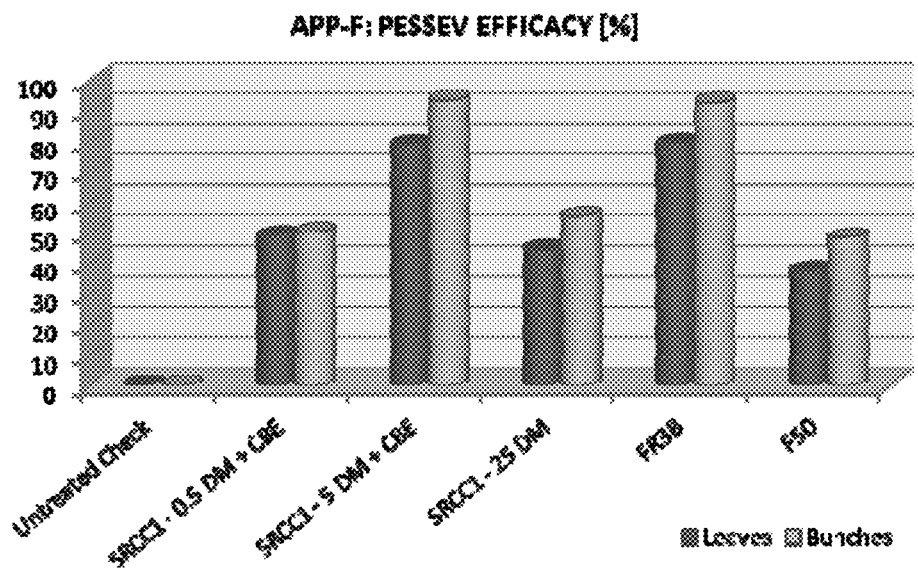
FIG. 2c: Results of PESSEV efficacy evaluation after application F.
Figure 3A:
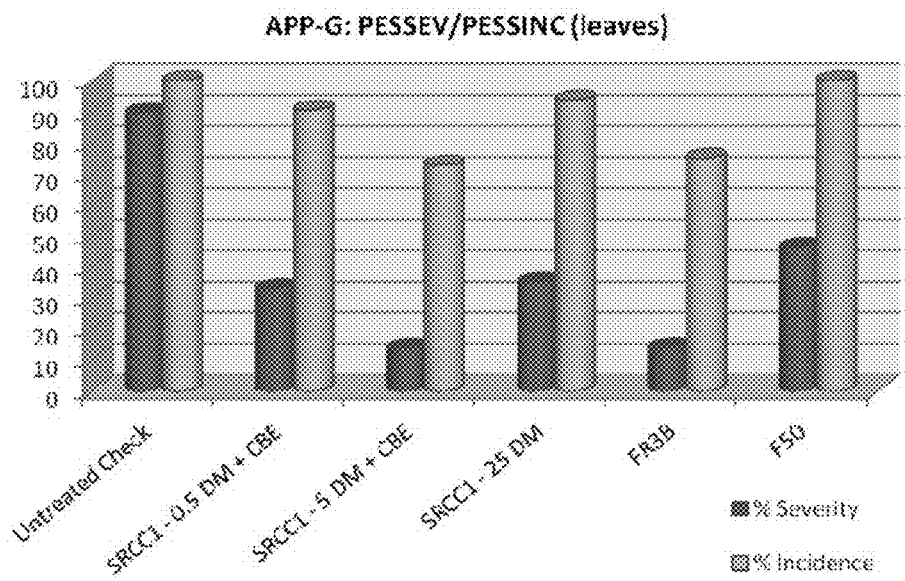
FIG. 3a: Results of the first assessment on leaves with regard to the pest severity PESSEV and the pest incidence PESINC after application G.
Figure 3B:
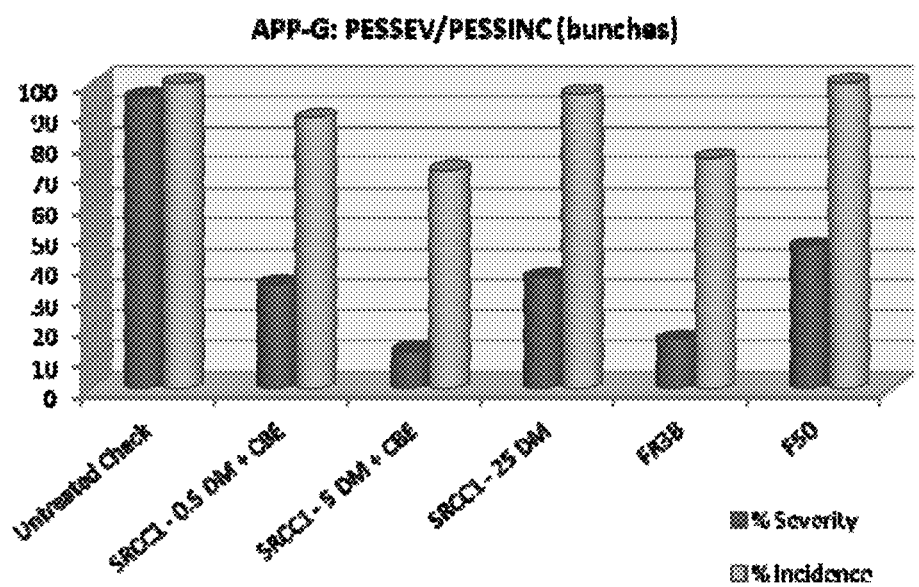
FIG. 3b: Results of the first assessment on bunches with regard to the pest severity PESSEV and the pest incidence PESINC after application G.
Figure 3C:
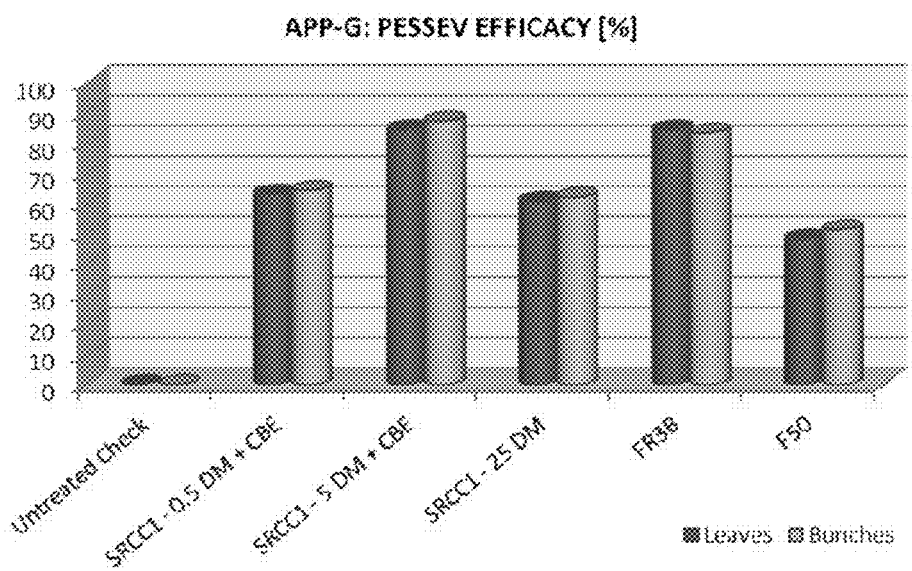
FIG. 3c: Results of PESSEV efficacy evaluation after application G.

The scope and interest of the invention may be better understood on basis of the following examples which are intended to illustrate embodiments of the present invention. However, they are not to be construed to limit the scope of the claims in any manner whatsoever.

Example 1—Preparation of Surface Reacted Calcium Carbonate (SRCC 1)

In a mixing vessel, 330 liters of an aqueous suspension of calcium carbonate-containing mineral was prepared by adjusting the solids content of a ground limestone calcium carbonate from Omya SAS, Orgon, having a weight based median particle size of 1.3 µm, as determined by sedimentation, such that a solids content of 10 wt.-%, based on the total weight of the aqueous suspension, was obtained.

Whilst mixing the suspension at a mixer tip speed of 12.7 m/s, 10.6 kg of an aqueous solution containing 30 wt.-% phosphoric acid, based on the total weight of the aqueous solution, was added to said suspension over a period of 12 minutes at a temperature of 70° C. After the addition of the acid, the slurry was stirred for additional 5 minutes, before removing it from the vessel and drying. During acid treatment, carbon dioxide was formed in situ in the aqueous suspension.

The resulting surface-reacted calcium carbonate SRCC1 had an intraparticle intruded specific pore volume of 0.871 $g/cm^3$ for the pore diameter range of 0.004 to 0.4 µm (using a Micromeritics Autopore IV 9500 mercury porosimeter having a maximum applied pressure of 414 MPa with a equilibration time used at each pressure step of 20 seconds; the sample material was sealed in a 5 ml chamber powder penetrometer for analysis), a volume median grain diameter ($d_{50}$) of 7.3 µm and a $d_{98}$ of 16.6 µm as measured by laser diffraction (Malvern Mastersizer 2 000) and a specific surface area of 52.1 $m^2/g$.

Example 2—Preparation of Compositions with Surface-Reacted Calcium Carbonate (SRCC) as Carrier In the present example, the surface reacted calcium carbonate (SRCC1) was loaded with different amounts of dimethomorph (DM). The dimethomorph was obtained from Chemos GmbH, Regenstauf, Germany, and had a purity of >98%.

The amounts of the reagents used can be derived from the below Table 1.

The respective amounts of DM listed in the below Table 1 were dissolved in 700 ml acetone (p.a. from Sigma-Aldrich) in a 2 liters Erlenmeyer flask at room temperature.

100 g of surface reacted calcium carbonate (SCRR1) powder were placed in a 5 liters round bottom flask and the DM/Acetone solution was added to the flask. Then the round bottom flask was mounted on a Rotavapor apparatus, the water bath of which having been heated to a temperature of 40° C. The rotation of the Rotavapor apparatus was started without applying any vacuum. After 30 minutes of rotation, the temperature of the water bath was raised to 45° C. and a vacuum of 470 mbar was applied. After the apparent evaporation of the acetone the vacuum was decreased to <50 mbar for at least 30 minutes to achieve a complete evaporation of the acetone. The surfaced reacted calcium carbonate powder loaded with the DM and also being dry was discharged from the flask and used for further trials.

TABLE 1

| | DM loading | |
|---|---|---|
| Sample No. | (g DM per 100 g SRCC1) | (wt.-% on total weight) |
| SRCC1-0.5 DM | 0.50 | 0.50 |
| SRCC1-5 DM | 5.26 | 5.00 |
| SRCC1-25 DM | 25.00 | 20.00 |

Example 3—Application Trials with Dimethomorph (DM)

The application trials were carried out in Piedmont, Italy. In these trials, three different dosage rates of three of the above-mentioned samples (SRCC1-0.5 DM, SRCC1-5 DM, SRCC1-25 DM) were applied against downy mildew on vineyard and the efficacy and selectivity thereof was evaluated. In addition, the performance in comparison to commercially available fungicides was also evaluated.

Agrochemical Compounds and Formulations Used in the Trials:

Cupravit® Bio Evolution (CBE): water soluble granules of tribasic copper sulfate (TBCS), from Bayer Cropscience Forum® R3B (FR3B): wettable powder, mixture of dimethomorph (DM) and tribasic copper sulfate (TBCS), from BASF Crop Protection Italia Forum® 50 WP (F50): wettable powder of dimethomorph, from BASF SRCC1-0.5 DM: according to Example 2

SRCC1-5 DM: according to Example 2

SRCC1-25 DM: according to Example 2

Trial Fungicide Treatments:

TABLE 2

| Trial No. | Treatment description | FO (w/w) | FO type | FO rate [kg/ha] | AI rate [kg AI/ha] | Appl. codes | Crop destr. |
|---|---|---|---|---|---|---|---|
| T1 | Untreated control | — | — | — | — | — | — |
| T2 | SRCC1-0.5 DM + CBE: | | | | | ABCDEFG | Y |
| | DM | 0.5% | WP | 4.2 | 0.021 | | |
| | TBCS (as CBE) | 30% | WG | 2.8 | 0.84 | | |
| T3 | SRCC1-5 DM + CBE: | | | | | ABCDEFG | Y |
| | DM | 5% | WP | 4.2 | 0.21 | | |
| | TBCS (as CBE) | 30% | WG | 2.8 | 0.84 | | |
| T4 | SRCC1-25 DM: | | | | | ABCDEFG | Y |
| | DM | 20% | WP | 1.25 | 0.25 | | |
| T5 | FR3B: | | WP | 3.5 | 1.05 | ABCDEFG | Y |
| | DM | 6% | | | 0.21 | | |
| | TBCS | 24% | | | 0.84 | | |
| T6 | F50: | 50% | WP | 0.5 | | ABCDEFG | Y |
| | DM | | | | 0.25 | | |

FO = formulation
AI = active ingredient
WP = wettable powder, i.e. a powder formulation to be applied as a suspension after dispersion in water
WG = water dispersable granulate, i.e a formulation consisting of granules to be applied after disintegration and dispersion in water
Y = Yes Trial Setup:
Replications: 4
Untreated treatments: 1 (no treatment at all for comparison reasons)
Conduct: Good Laboratory Practice (GLP)
Good Experimental Practice (GEP); GEP with no protection
Design: Randomized Complete Block (RCB)
Treatment units: Treated "Plot" experimental unit size;
unit size width: 2.5 meters
unit size length: 13.5 meters
Application volume: 700l/ha (liquid used: water)
Mix size: 12 liters The efficacy against *Plasmopara viticola* and the selectivity on the crop of the test products SRCC1-0.5 DM and SRCC1-5 DM both applied in mixture with tribasic copper sulfate (Cupravit Bio Evoluion WG), respectively, in treatments T2 and T3, were evaluated. These test products were compared with FR3B as a reference in treatment T5.

The efficacy of SRCC1-25 DM was also evaluated in treatment T4 and compared with the reference F50 sprayed in treatment T6.

Seven experimental applications (ABCDEFG) were done during the whole trial period with test and reference products. The spray interval was 10 to 12 days, depending on the meteorological conditions. The application details are described in Table 3 and Table 4 below.

TABLE 3

| | Application description | | | | | | |
|---|---|---|---|---|---|---|---|
| | A | B | C | D | E | F | G |
| Appl. date | 8/5/2014 | 20/5/2014 | 29/5/2014 | 10/6/2014 | 20/6/2014 | 30/6/2014 | 10/7/2014 |
| Start time | 8:40 | 17:00 | 15:00 | 8:10 | 14:30 | 13:00 | 7:30 |
| Stop time | 9:30 | 18:00 | 15:40 | 8:45 | 15:30 | 14:00 | 8:30 |
| Appl. method | SPRAY | SPRAY | SPRAY | SPRAY | SPRAY | SPRAY | SPRAY |
| Appl. placement | BROFOL | BROFOL | BROFOL | BROFOL | BROFOL | BROFOL | BROFOL |
| Operator name | PV, DP | DR, DP | DP, DR | DP, PV | PV, DP | DR, DP | DP, DR |
| Air temp. [° C.] | 13.3 | 19.0 | 24.0 | 23.5 | 27.4 | 30.0 | 21.4 |
| RH [%] | 83 | 68 | 59 | 61 | 47 | 50 | 57 |
| Wind [m/s] | 0.0 | 0.0 | 0.0 | 0.0 | 0.0 | 0.0 | 0.0 |
| Dew (Y/N) | N | N | N | N | N | N | N |
| Soil moisture | WET | DRY | WET | DRY | WET | DRY | WET |
| Cloud cover [%] | 90 | 100 | 40 | 90 | 0 | 0 | 0 |
| Next moisture | 19/5/2014 | 22/5/2014 | 31/5/2014 | 13/6/2014 | 25/6/2014 | 1/7/2014 | 12/7/2014 |
| Δt next moisture [d] | 11 | 2 | 2 | 3 | 5 | 1 | 1 |

TABLE 4

| Application equipment | | | | |
|---|---|---|---|---|
| | A, B | C | D | E, F, G |
| Equipment Type | KNAMOT | KNAMOT | KNAMOT | KNAMOT |
| Operation Pressure [kPa] | 1 200 | 1 200 | 1 200 | 1 200 |
| Nozzle Type | Flat fan | Flat fan | Flat fan | Flat fan |
| Nozzle Size | Yamaho D6 | Yamaho D6 | Yamaho D6 | Yamaho D6 |
| Nozzle spacing [cm] | 2 | 2 | 2 | 2 |
| Nozzles per row | 2 | 2 | 2 | 2 |
| Calibration [ml/min] | 2 000 | 2 000 | 2 000 | 2 000 |
| Row sides applied | 2 | 2 | 2 | 2 |
| Carrier substance | WATER | WATER | WATER | WATER |
| Spray volume [l/ha] | 300 | 400 | 500 | 700 |
| Mix size [l] | 5 | 7 | 9 | 12 |
| Propellant type | PUMP | PUMP | PUMP | PUMP |
| Tank Mix (Y/N) | Y | Y | Y | Y |

The first symptoms of Plasmopara viticola were observed on the untreated control leaves and bunches (T1) in the middle of June as a result of the favorable meteorological conditions. Because of the frequent rainfall in June and July, the disease developed quickly on leaves and bunches. In terms of disease development, the most important rainfalls were those of middle of June.

In this trial according to the present invention, the disease pressure was assessed through two standard parameters:
(i) PESSEV=the pest severity (i.e. the intensity) determined as infected area per bunch or leaf in %; and
(ii) PESINC=the pest incidence (i.e. the frequency) determined in % of bunches and leaves infected.

These two parameters were used to calculate the efficacies of the agrochemical composition as follows:

PESSEV efficacy [%]=(PESSEV$_{untreated}$−PESSEV$_{treated}$)/PESSEV$_{untreated}$×100

PESINC efficacy [%]=(PESINC$_{untreated}$−PESINC$_{treated}$)/PESINC$_{untreated}$×100.

Results:

First assessment was performed on Jun. 18, 2014. On the untreated control leaves was noticed 16.2% of downy mildew severity and 76.4% of incidence, while on bunches, severity and incidence were 61.0% and 98.0%, respectively. All the treatments showed a good disease control, differing significantly from untreated control.

On severity, both on leaves and bunches, treatment T2 (SRCC1-0.5 DM+CBE) and T3 (SRCC1-5 DM+CBE) did not show significant difference to the reference T5 (FR3B). On incidence, both on leaves and bunches, treatment T3 (SRCC1-5 DM+CBE) did not show significant difference from the reference while T2 (SRCC1-0.5 DM+CBE) showed a lower level of disease control than the reference. On leaves and bunches, treatment T4 (SRCC1-25 DM) did not show significant differences to the reference T6 (F50).

The second assessment was made on Jun. 30, 2014. On the untreated control leaves was noticed 49.7% of downy mildew severity and 92.3% of incidence, while on bunches severity and incidence were 76.1% and 98.3%, respectively. In terms of severity, both on leaves and bunches, all the treatments differed only numerically from the untreated control.

On incidence, both on leaves and bunches, treatment T2 (SRCC1-0.5 DM+CBE) and T3 (SRCC1-5 DM+CBE) did not show any difference to the reference T5 (FR3B). On severity, both on leaves and bunches, treatment T3 (SRCC1-5 DM+CBE) did not show numerical difference to the reference while T2 (SRCC1-0.5 DM+CBE) showed a lower disease control as compared to the reference.

On leaves and bunches, treatment T4 (SRCC1-25 DM) did not show any numerical differences to the reference T6 (F50).

The third assessment was made on Jul. 18, 2014. On the untreated control leaves was noticed 89.5% of downy mildew severity and 100.0% of incidence, while on bunches severity and incidence were 95.4% and 100.0%, respectively. In terms of severity, both on leaves and bunches, all the treatments differed numerically from the untreated control.

On incidence, both on leaves and bunches, treatment T2 (SRCC1-0.5 DM+CBE) with 90.5% (leaves) and 88.8% (bunches) and T3 (SRCC1-5 DM+CBE) with 72.8% (leaves) and 71.5% (bunches) did not show any numerical difference to the reference T5 (FR3B) that showed 75.0% and 75.3% on leaves and bunches, respectively. On severity, both on leaves and bunches, treatment T3 (SRCC1-5 DM+CBE) with 13.9% (leaves) and 12.2% (bunches) did not show any numerical difference to the reference that showed 14.1% and 15.9% on leaves and bunches, respectively, while T2 (SRCC1-0.5 DM+CBE) with 33.1% (leaves) and 34.1% (bunches) showed a lower level of disease control as compared to the reference.

On leaves, treatment T4 (SRCC1-25 DM) with 35.2% of severity and 93.8% of incidence did not show significant differences as compared to the reference T6 (F50) that showed 46.3% of severity and 100.0% of incidence. On bunches, treatment T4 (SRCC1-25 DM) with 36.3% of severity and 96.5% of incidence did not show significant differences to the reference T6 (F50) that showed 46.6% of severity and 100.0% of incidence.

A significant dosage rate effect could be observed for dimethomorph as active ingredient (AI) between T2 (SRCC1-0.5 DM+CBE at 0.021 kg DM/ha) and T3 (SRCC1-5 DM+CBE at 0.21 kg DM/ha) both on leaves and bunches.

CONCLUSION

The data of this trial revealed a good downy mildew control provided by test the products SRCC1-0.5 DM, SRCC1-5 DM, and SRCC1-25 DM according to the present invention in terms of disease incidence in presence of a very high degree of disease attack (85.4% of leaves severity and 87.4% of bunches severity).

No significant difference between SRCC1-5 DM+CBE and FR3B could be observed while SRCC1-0.5 DM+CBE showed a lower level of disease control than FR3B.

A significant dosage rate effect could be observed for dimethomorph as active ingredient (AI) between T2 (SRCC1-0.5 DM+CBE at 0.021 kg DM/ha) and T3 (SRCC1-5 DM+CBE at 0.21 kg DM/ha) both on leaves and bunches.

No significant difference between SRCC1-25 DM (T4) and F50 (T6) could be observed.

A significant effect of copper could be observed in downy mildew control. No phytotoxic symptoms were observed on grapevine leaves and bunches (Dolcetto variety) in all the treatments where the test and reference products were applied.

The invention claimed is:

1. A composition comprising:
   (a) a particulate solid carrier comprising a surface-reacted calcium carbonate that is a reaction product of calcium carbonate in an aqueous medium with carbon dioxide and at least one water soluble strong acid or medium strong acid, wherein the carbon dioxide is formed in situ and/or supplied from an external source; and
   (b) at least one agrochemical compound loaded onto the particulate solid carrier;
   wherein the at least one agrochemical compound is a fungicide selected from the group consisting of benalaxyl, kiralaxyl, furalaxyl, metalaxyl, mefenoxam, oxadixyl, ofurace, dimethomorph, flumorph, pyrimorph, benthiavalicarb, iprovalicarb, valifenalate, and mandipropamid.

2. The composition according to claim 1, wherein the composition further comprises a copper source that is optionally loaded onto the particulate solid carrier.

3. The composition according to claim 2, wherein the copper source is tribasic copper sulfate or tribasic copper chloride.

4. The composition according to claim 1, wherein the agrochemical compound is dimethomorph.

5. The composition according to claim 1, wherein the particulate solid carrier and the agrochemical compound are present in the composition at a weight ratio of from 1,000:1 to 1:1.

6. The composition according to claim 1, wherein the particulate solid carrier and the agrochemical compound are present in the composition at a weight ratio of from 500:1 to 2:1.

7. The composition according to claim 1, wherein the particulate solid carrier and the agrochemical compound are present in the composition at a weight ratio of from 200:1 to 3:1.

8. The composition according to claim 1, wherein the calcium carbonate is a calcium carbonate-containing mineral selected from the group consisting of marble, chalk, dolomite, limestone, and an any mixture thereof; and/or a precipitated calcium carbonate having one or more of an aragonitic, vateritic and calcitic crystal form.

9. The composition according to claim 1, wherein the particulate solid carrier has a $d_{50}$ of from 2 to 50 μm.

10. The composition according to claim 1, wherein the particulate solid carrier has a specific surface area of from 10 to 200 $m^2/g$.

11. The composition according to claim 1, wherein the particulate solid carrier has an intraparticle intruded specific pore volume within a range of 0.15 to 1.3 $cm^3/g$, calculated from a mercury intrusion porosimetry measurement.

12. The composition according to claim 1, wherein the surface-reaction calcium carbonate is a reaction product of a calcium carbonate-containing material selected from the group consisting of marble, chalk, dolomite, limestone, and any mixture thereof in an aqueous medium with carbon dioxide and with phosphoric acid, wherein the carbon dioxide is formed in situ, and wherein the agrochemical compound is dimethomorph.

13. A process for the preparation of the composition according to claim 1 comprising:
   a) providing the particulate solid carrier comprising the surface-reacted calcium carbonate;
   b) providing the at least one agrochemical compound; and
   c) loading the at least one agrochemical compound on the particulate solid carrier comprising the at least one surface-reacted calcium carbonate.

14. The process according to claim 13, wherein the surface-reaction calcium carbonate is a reaction product of a calcium carbonate-containing material selected from the group consisting of marble, chalk, dolomite, limestone, and any mixture thereof in an aqueous medium with carbon dioxide and with phosphoric acid, wherein the carbon dioxide is formed in situ, and wherein the agrochemical compound is dimethomorph.

15. A process for treating a plant with a fungicide comprising applying to the plant a composition comprising:
   (a) a particulate solid carrier comprising a surface-reacted calcium carbonate that is a reaction product of calcium carbonate in an aqueous medium with carbon dioxide and at least one water soluble strong acid or medium strong acid, wherein the carbon dioxide is formed in situ and/or supplied from an external source; and
   (b) at least one agrochemical compound loaded onto the particulate solid carrier;
   wherein the at least one agrochemical compound is a fungicide selected from the group consisting of benalaxyl, kiralaxyl, furalaxyl, metalaxyl, mefenoxam, oxadixyl, ofurace, dimethomorph, flumorph, pyrimorph, benthiavalicarb, iprovalicarb, valifenalate, and mandipropamid.

16. The process according to claim 15, wherein the surface-reaction calcium carbonate is a reaction product of a calcium carbonate-containing material selected from the group consisting of marble, chalk, dolomite, limestone, and any mixture thereof in an aqueous medium with carbon dioxide and with phosphoric acid, wherein the carbon dioxide is formed in situ, and wherein the agrochemical compound is dimethomorph.

17. The process according to claim 15, wherein the composition is used to treat and/or prevent a fungus or fungus-like organism.

18. The process according to claim 17, wherein the fungus or fungus-like organism is an oomycete.

19. The process according to claim 17, wherein the fungus or fungus-like organism is *Perenosporales*.

20. The process according to claim 18, wherein the fungus or fungus-like organism is *Plasmopara viticola*.

21. The process according to claim 15, wherein the plant is selected from the group consisting of a potato plant, a tomato plant, a corn plant, a tobacco plant and a grapevine.

22. The process according to claim 15, wherein the plant is a grapevine.

23. The process according to claim 15, wherein the particulate solid carrier enhances efficacy of the agrochemical compound loaded onto the carrier.

24. The process according to claim 23, wherein the efficacy is a PESSEV (pest severity) efficacy and/or a PESINC (pest incidence) efficacy.

* * * * *